United States Patent [19]
van Krieken et al.

[11] Patent Number: 5,782,887
[45] Date of Patent: Jul. 21, 1998

[54] PACEMAKER SYSTEM WITH PAC TRACKING BASED ON QT DATA

[75] Inventors: Frits M. van Krieken; Johannes S. van der Veen, both of Dieren, Netherlands

[73] Assignee: Vitatron Medical, B.V., Dieren, Netherlands

[21] Appl. No.: 824,765

[22] Filed: Mar. 26, 1997

[51] Int. Cl.[6] ................................................ A61N 1/362
[52] U.S. Cl. ............................................................ 607/25
[58] Field of Search .................................. 607/25, 14, 9

[56] References Cited

U.S. PATENT DOCUMENTS

| | | |
|---|---|---|
| 4,527,568 | 7/1985 | Rickards ............................ 607/25 |
| 4,593,695 | 6/1986 | Wittkampf . |
| 4,932,406 | 6/1990 | Berkovits . |
| 5,247,930 | 9/1993 | Begemann et al. ................. 607/11 |

*Primary Examiner*—Scott M. Getzow
*Attorney, Agent, or Firm*—Woodcock Washburn Kurtz Mackiewicz & Norris LLP

[57] ABSTRACT

A dual chamber pacemaker system and method provide for safe tracking of PACs. The pacemaker obtains an indication of when the T-wave has occurred within the cycle when the PAC occurs, either by measuring the T wave during the cycle, or by getting a QT interval measure from one or more prior cycles. The pacemaker determines a safe V—V interval as the QT interval measure plus a safety factor, the safety factor being selected so as to insure that a pulse that tracks the PAC does not get delivered during the vulnerable period. A PAC is tracked if and only if the VA interval plus the AV delay is as great as the safe V—V interval.

20 Claims, 13 Drawing Sheets

PACEMAKER SYSTEM WITH PAC TRACKING BASED ON QT DATA

FIELD OF THE INVENTION

This invention relates to implantable dual chamber cardiac pacemakers with the capability of delivering ventricular pace pulses synchronized to sensed atrial beats and, more particularly, dual chamber pacemakers which can determine and respond to the occurrence of a premature atrial contraction.

BACKGROUND OF THE INVENTION

A dual chamber pacemaker, e.g., a DDD pacemaker, provides the advantageous feature of being able to track atrial heartbeats, i.e., provide a ventricular pace pulse which follows the natural atrial beat by an atrio-ventricular (AV) interval which simulates the delay of a healthy heart between the P-wave and the ventricular depolarization. Such atrial tracking provides the cardiac synchrony of a healthy heart, and is thus a substantial benefit to the patient. While pacemaker design attempts to maximize the tracking of atrial beats, it is recognized that not all atrial senses are to be tracked. Thus, if atrial senses arrive at too great a rate, or are otherwise not physiological, it can be harmful to track them. For this reason, most pacemakers impose a high rate limit, or tracking limit, which controls the rate at which the ventricle can be paced.

A particularly bothersome situation is the occurrence of a premature atrial contraction, or PAC. As used herein, a PAC is defined as a first atrial beat that arrives after an atrial interval shorter than to tachycardia interval. Thus, if tachycardia is defined as a rhythm with a rate greater than 130 bpm, an atrial beat at an interval less than that which corresponds to 130 bpm is a PAC if no other such tachy beat has preceded it. If true tachycardia is present, steps designed to deal specifically with breaking it up are called for. But, if there is a PAC that stands alone, it is important to deal with it in the most effective way. If a dual chamber pacemaker does not properly react to a PAC, there is a danger of pacemaker mediated tachycardia (PMT). For this reason, but even without that problem, it is desirable not to just ignore the PAC, but to pace the ventricle in a tracking relation if possible. But if the PAC has occurred close enough to the last ventricular event, a ventricular pace that is delivered at the time out of an AV delay after the PAC could fall in the cardiac vulnerable period, which can lead to fibrillation. To avoid this dangerous possibility, many pacemakers incorporate a post ventricular atrial refractory period, or PVARP, which is long enough to prevent the pacemaker from sensing and responding to any atrial sense that occurs close to the ventricular vulnerable period. The problem with this solution is that the pacemaker is prevented from tracking certain high rate atrial signals, PAC or otherwise, which could be safely tracked.

There thus has remained a need in the pacemaker art for a pacemaker design and method for tracking PACs whenever it is safe to do so. This invention provides such a feature, and is grounded on the observation that the end of the vulnerable period corresponds to the sensing of the ventricular repolarization, or the T-wave. By determining the time relation of the proposed ventricular pace pulse which is to track the PAC to the expected or sensed T-wave, the pacemaker can determine whether delivery of the pace pulse is safe.

SUMMARY OF THE INVENTION

It is an object of the invention to provide a pacemaker system and method for optimally tracking PACs whenever this can be done safely. Thus, it is an object to provide an implantable dual chamber pacemaker that can identify the occurrence of a PAC, determine whether a synchronized ventricular pace pulse could be delivered at a safe time after the ventricular vulnerable period, and deliver a synchronized ventricular pace pulse whenever it would be delivered safely after such vulnerable period. The invention is applicable for all atrial tracking modes, e.g., DDD, VDD, VAT.

In accordance with the above object, this invention provides a dual chamber pacemaker which senses P waves from the patient's atrium, and QRS and T waves from the patient's ventricle. The pacemaker identifies the occurrence of a PAC, and determines whether a ventricular pace pulse delivered at the time out of an AV delay following the PAC would be after the T wave by a predetermined safety margin, and thus be safely after the vulnerable period. In a first preferred embodiment, the expected time of the T wave for the cycle in which the PAC occurs is determined by examining values of the QT interval for one or more prior cycles, and a V to V safety interval of QT_int+SM, where SM is a safety margin, is calculated; the tracking ventricular pace pulse can be delivered if but only if it were to be delivered at or after the end of the safety interval.

As used herein, the QT interval refers to either the interval between a delivered ventricular stimulus (VP) and the following T-wave, or the interval between a V-sense and a T-wave. In a second preferred embodiment, when a PAC is detected, the pacemaker determines the timing of the sensed T wave for the same cycle, and enables the tracked ventricular pace pulse only if it is not to be delivered before time out of a safety margin interval after the T wave.

DESCRIPTION OF THE PREFERRED EMBODIMENTS

Figure 1:
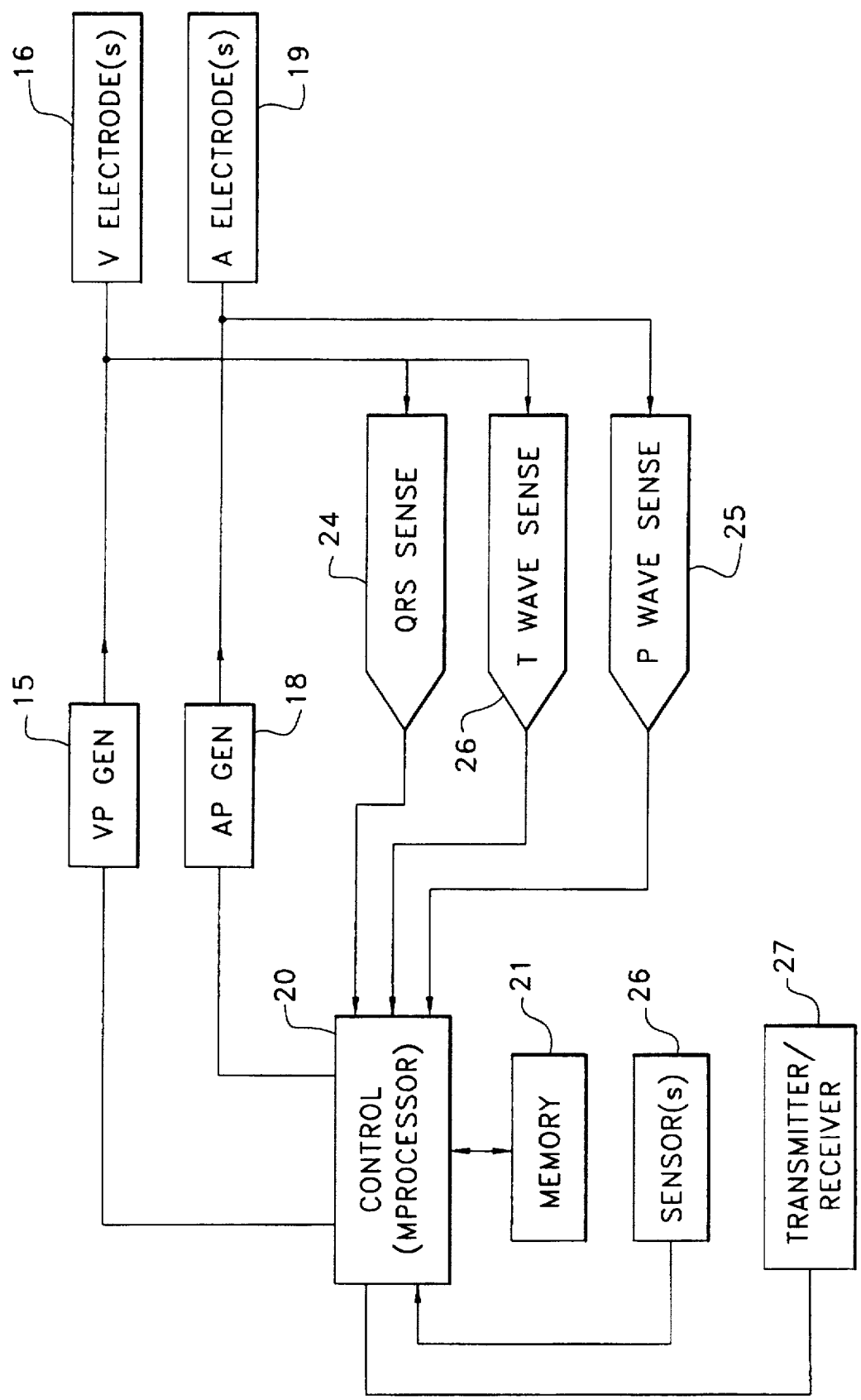
FIG. 1 is a block diagram of the primary components of a pacemaker in accordance with this invention.

Referring now to FIG. 1, there is shown a simplified block diagram of the primary components of a pacemaker as used in the system and method of this invention. The dual chamber pacemaker illustrated follows the general logic and decisional rules as described in U.S. Pat. No. 5,247,930, incorporated herein by reference. A ventricular pace generator is illustrated at 15 for generating and delivering ventricular pace pulses under control of control unit 20, in a known fashion. The ventricular pace pulses are delivered to one or more ventricular electrodes illustrated at 16. Likewise an atrial pace generator is illustrated at 18, which generates atrial pace pulses under control of unit 20 and delivers the atrial pace pulses to one or more atrial electrodes as illustrated at 19. Sense signals from the ventricular electrode or electrodes are connected to QRS sense amplifier 24 and T-wave sense amplifier 26, the outputs of which are inputted to control block 20 for processing. Although not shown, it is understood that by those of skill in the pacemaker art that the input amplifiers 24, 26 are controlled in terms of sensitivity and timing by control unit 20. Likewise, signals detected in the atrium by electrodes 19 are delivered to P-wave sense amplifier 25, the output of which is connected through to control 20.

Control block 20 suitably incorporates a microprocessor with associated software, the software being stored in memory 21, as indicated. Memory 21 may contain RAM and ROM, and the assignment of pacemaker functions can be divided between hardware and software in any desired manner. In the preferred embodiment of this invention, the algorithms are suitably carried out under software control. One or more sensors 26 may be provided to continuously detect rate-indicating parameters, the parameter signals being inputted to control block 20 to provide rate responsive control, in a known manner. Alternately, as in the preferred embodiment, a rate responsive parameter is QT interval, which is determined by control 20 by timing the duration between a delivered stimulus (VP) and the following T wave. Thus, in the context of this invention, the rate responsive control may suitably vary pacing rate between an upper rate limit (URL) and a lower rate limit (LRL) in a known fashion, subject to the rules discussed below. As illustrated at 27, the pacemaker suitably has a transmitter/receiver for receiving programmer communications from an external programmer, and for transmitting collected data back to a transmitter, in a known fashion.

Figure 2A:
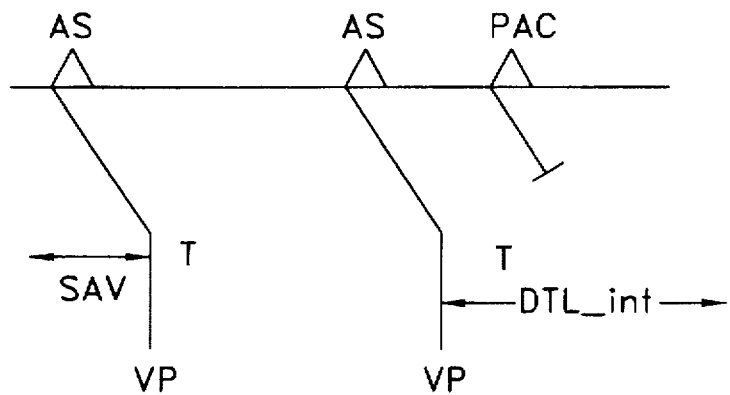
FIG. 2A is a timing diagram indicating tracking of atrial cardiac signals where the dynamic tracking limit is set to a predetermined rate above the patient's atrial physiological rate.

Referring now to FIG. 2A, there is shown a timing diagram for a dual chamber pacemaker where the atrial sense (AS) is tracked by delivery of a ventricular pace (VP) at an AV interval following the AS, as long as the delivered VP is at a rate below the tracking limit. As used herein, the terms "track" or "tracking" refer to delivering a VP in synchronized relation to an AS. In a pacemaker operating in accordance with the above-referenced U.S. Pat. No. 5,247, 930, a running measure of physiological atrial rates is calculated as phys_rate; the tracking limit, or highest rate at which a VP can be delivered, is referred to as the dynamic tracking rate, and is determined as the varying physiological rate plus K, where K is suitably 15 bpm, e.g., phys_rate+15 bpm. As shown in FIG. 2A, the first two AS events are followed by delivery of tracking VPs. The next atrial event is a PAC, and it is shown as occurring at about the time of the T-wave that follows the second illustrated VP, and clearly before timeout of the interval corresponding to dynamic tracking limit. In this situation, the PAC is not tracked.

Figure 2B:
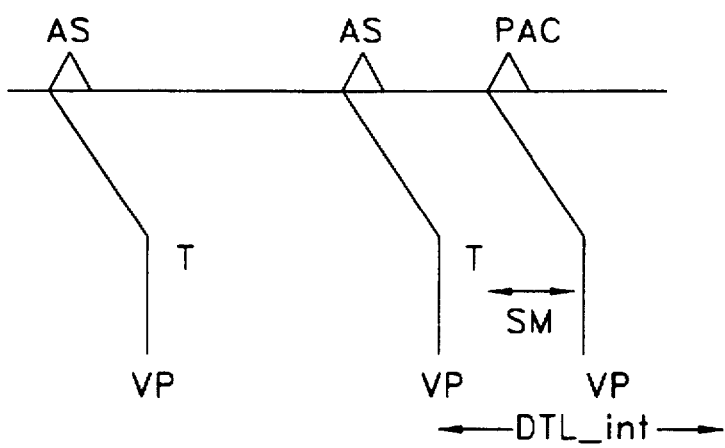
FIG. 2B is a timing diagram illustrating how a PAC can be tracked by delivery of a ventricular pulse as long as it can be delivered at at least a safe interval following the last ventricular stimulus.
Figure 2C:
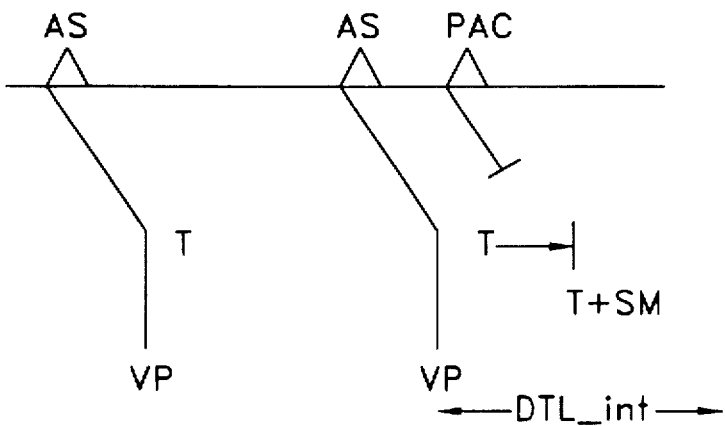
FIG. 2C is a timing diagram similar to FIG. 2B, but illustrating the situation where the PAC arrives so early that it cannot be safely tracked because the ventricular pulse would be delivered before timeout of the ventricular safety interval, in accordance with this invention.

Referring to FIG. 2B, there is shown a timing diagram where the third atrial sense is again a PAC, but wherein the PAC is tracked even though it arrives before the timeout of the DTL interval. In this situation, while the PAC arrives at about the time of the T-wave following the last delivered VP, the VP can be delivered upon timeout of the AV interval after the PAC, since VP is delivered after timeout of a predetermined safety margin following the T-wave. Here, the AV escape interval times out after an interval following the last VP defined as safe_VV_int=QT_int+SM, such that it is safe to deliver a tracking VP. By contrast, in FIG. 2C, the PAC arrives sufficiently earlier that timeout of the AV escape interval occurs before timeout of the safe_VV_int, such that delivery of a tracking VP is blocked. This illustrates the primary feature of the invention, namely utilization of a calculated V—V interval which extends safely beyond the T-wave by a safety margin (SM), so as to be used as a timing point for determining whether the PAC can be tracked. The timing of the T-wave, as illustrated in FIGS. 2A–2C by the symbol "T", may either be a calculated time, as utilized in the first preferred embodiment illustrated in FIGS. 3–7; or an actual measured T-wave time, as utilized in the second preferred embodiment illustrated in FIGS. 8–11. It is noted that although the timing diagrams of FIG. 2B shows the prior ventricular event as a VP, it could also have been a VS.

Figure 3:
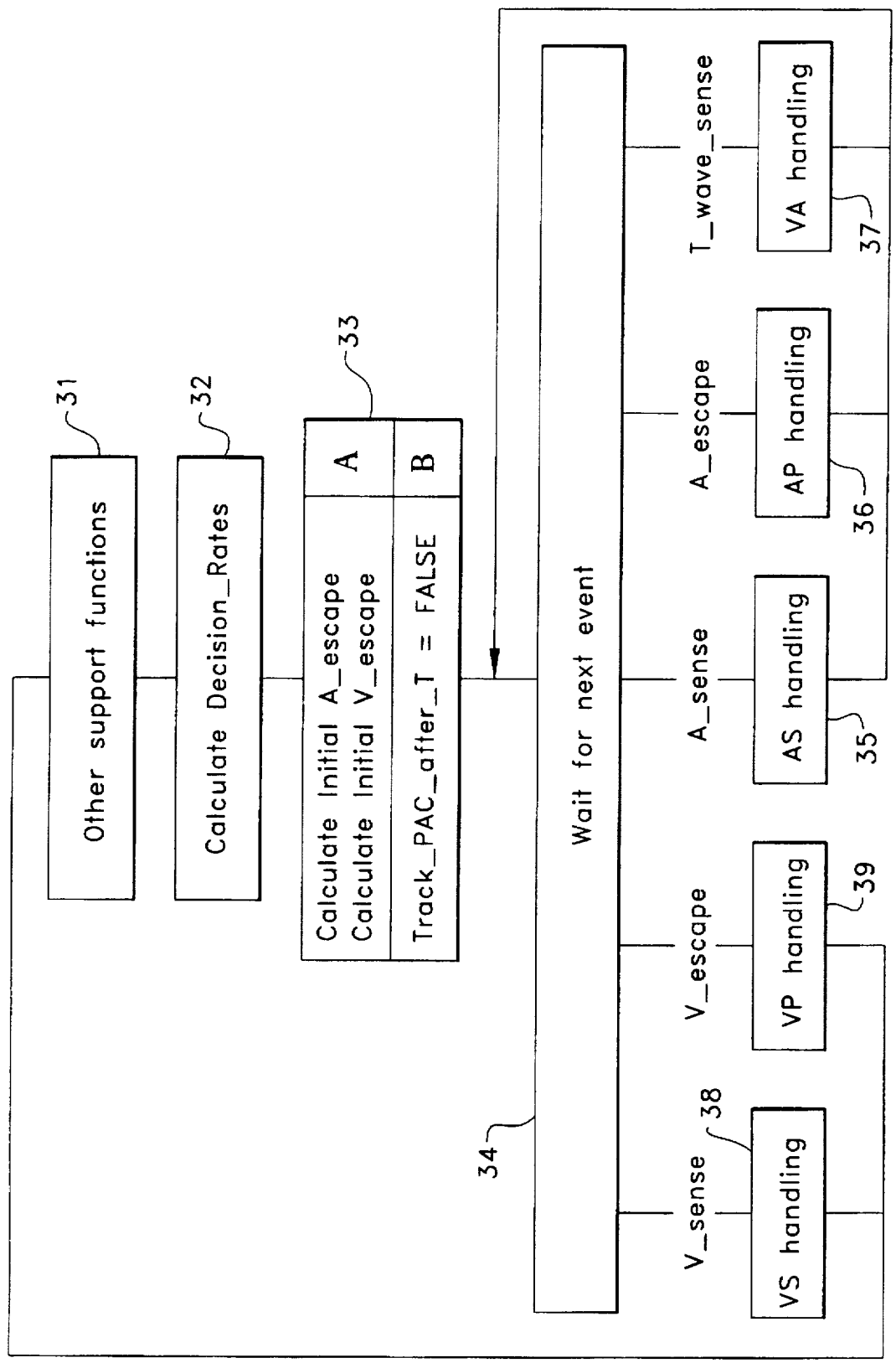
FIG. 3 is an overall flow diagram showing the primary operations which are performed each pacemaker cycle in a pacemaker in accordance with this invention.

Referring now to FIG. 3, there is shown an overall flow diagram of the primary operations carried out in a pacemaker in accordance with this invention. It is to be understood that most of the calculation-type operations are suitably software controlled, as discussed above in connection with FIG. 1. The operations illustrated in FIG. 3 are carried out cyclically. At 31, the pacemaker performs support functions which are not directly involved in this invention, although they may be integral to other features of the pacemaker operation. At block 32, the pacemaker calculates certain decision rates, as are disclosed in referenced U.S. Pat. No. 5,247,930, and which are discussed further in relation to FIG. 4A below. At block 33, for both the first and second preferred embodiments, the pacemaker calculates an initial atrial escape interval A_escape, and initial ventricular escape interval, V_escape. At this point, for the second embodiment, as designated in B in block 33, the pacemaker also sets a flag designated track_PAC_after_T=FALSE, for purposes discussed below in connection with FIGS. 8–11. Following this, the pacemaker is ready for an event, and proceeds to 34. The next event can be any one of the five events illustrated. If there has been an A_sense of a natural atrial beat, the pacemaker goes to the AS handling routine illustrated at 35, following which it goes back to block 34 and waits for a ventricular event. If there has been a timeout of the A_escape interval, the pacemaker goes to routine 36, AP handling, and after delivering an atrial pulse goes back to step 34. If there has been a T_wave_sense, the pacemaker goes to TS handling routine 37, following which it goes back to block 34. When and if there is then a V_sense, the pacemaker goes to V_sense handling routine 39, following which the cycle has been completed and the flow goes back to block 31. Likewise, if there has been a timeout of the V_escape interval, the pacemaker goes to routine 38 for VP handling, which culminates in delivery of a ventricular pace pulse, following which the routine goes to back to block 31.

Figure 4A:
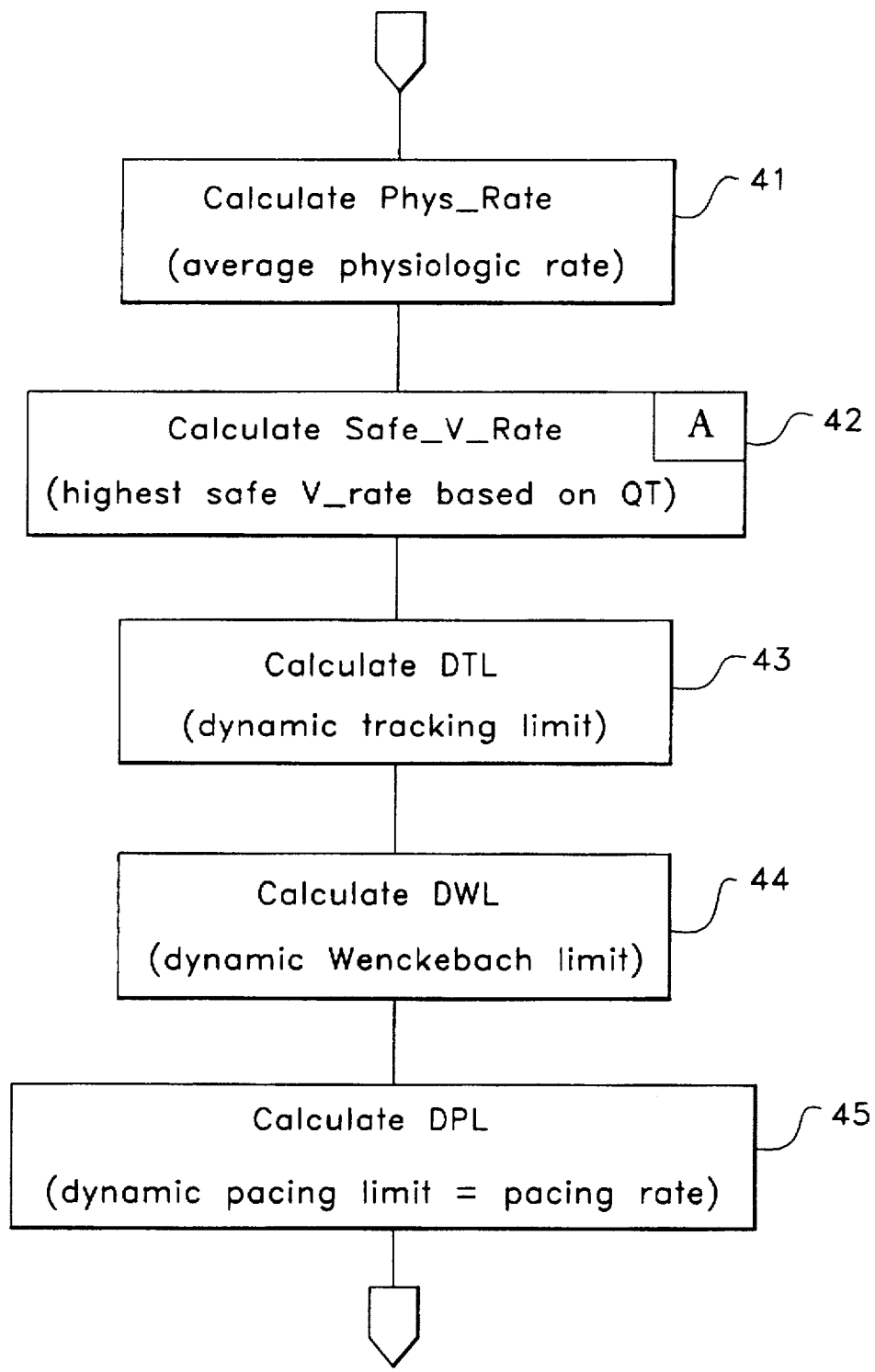
FIG. 4A is a flow diagram illustrating the determination of decision rates for use in controlling pacemaker functions in accordance with this invention.

Referring now to FIG. 4A, there is shown a flow diagram for calculating decision rates, corresponding to block 32 of FIG. 3. Reference is made to U.S. Pat. No. 5,247,930, for a detailed discussion of the decision rates and their use in controlling pacemaker operation. At 41, the pacemaker calculates phys_rate, which is a measure of the average physiological sinus rate. For example, this may be a running average of atrial rates which are within a defined physiological range. At block 42, for the first preferred embodiment as designated A, the pacemaker calculates a safe_V_rate, which is the highest safe ventricular rate that could be used, and which is based on QT interval as discussed further below in connection with FIG. 4B. For a second preferred embodiment, as disclosed in FIGS. 8–11, the safe_V_rate is not calculated at this time. Following this, at 43, the dynamic tracking limit (DTL) is calculated, as illustrated in the discussion relating to FIG. 4C. At 44, a dynamic Wenckebach limit (DWL) is calculated. Finally, at 45, the pacemaker calculates a dynamic pacing limit (DPL), which is the pacing rate at which pace pulses are delivered in the absence of natural heartbeats.

Figure 4B:
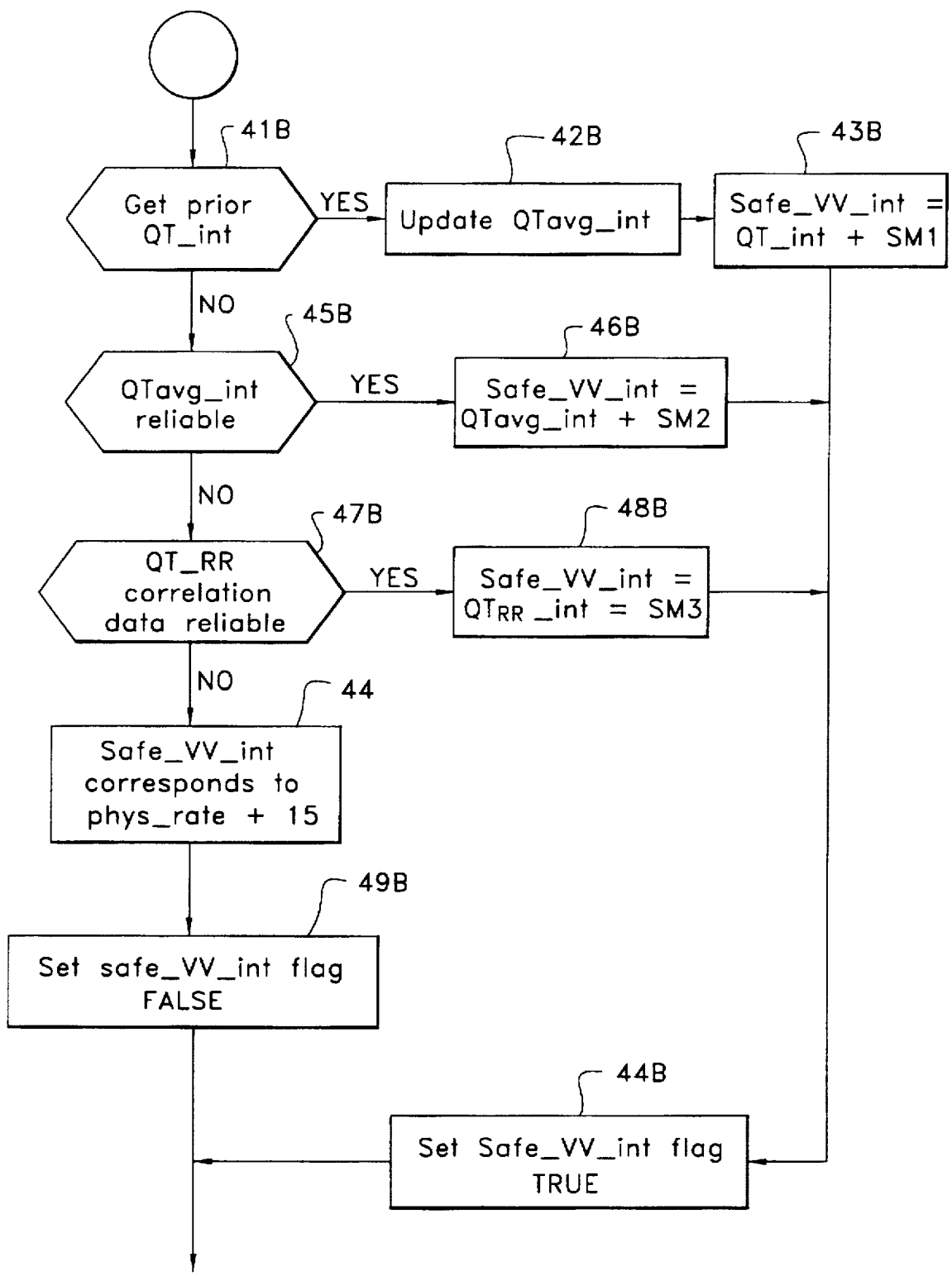
FIG. 4B is a flow diagram illustrating the calculation of the safety interval, or "safe_VV_int" in accordance with this invention.

Referring now to FIG. 4B, at block 41B it is determined whether the QT interval, QT_int, was obtained during the prior cycle. If yes, the routine branches to 42B and updates a running average of QT interval, $QT_{AVG}$_int. Then, at 43B, the safe ventricular interval, safe_V_int, is set equal to QT_int+a safety margin factor, SM1. SM1 may be programmed, or it may be a dynamic variable depending, for example, on rate. Following this, at 44B the safe_VV_int flag is set to TRUE. Going back to 41B, if there was no QT interval obtained in the last cycle, then the routine goes to 45B and determines whether $QT_{AVG}$_int is reliable for use this cycle. One way of determining such reliability is to keep track of the variation of $QT_{AVG}$, and if the variation over the most recent n cycles has been within a predetermined range, then it is deemed reliable. If the answer at 45B is yes, the routine goes to 46B and sets safe_VV_int equal to $QT_{AVG}$_int+SM2. SM2 is suitably slightly larger than SM1, based on the proposition that $QT_{AVG}$_int is not quite as good a predictor of where the T-wave will fall in the current cycle, as is the value of QT_int for the last cycle. Coming back to 45B, if the $QT_{AVG}$_int is not reliable, the routine goes to 47B and determines whether rate responsive correlation data is reliable. The rate correlation data is stored in memory for a rate responsive pacemaker which utilizes QT as a rate response parameter. If the data is a reliable option, the routine branches to 48B and sets safe_VV_int equal to $Q_{RR}$_int+SM3, where $QT_{RR}$_int is the QT interval that corresponds to the present rate, and SM3 is suitably larger than SM2. If, at 47B, it is determined that the RR correlation data is not reliable, the routine goes to block 44, and sets Save_VV_int to correspond to the phys_rate plus 15 bpm. After this, the safe_VV_int flag is set to FALSE at 49B, indicating that there is no usable value of safe_VV_int.

Figure 4C:
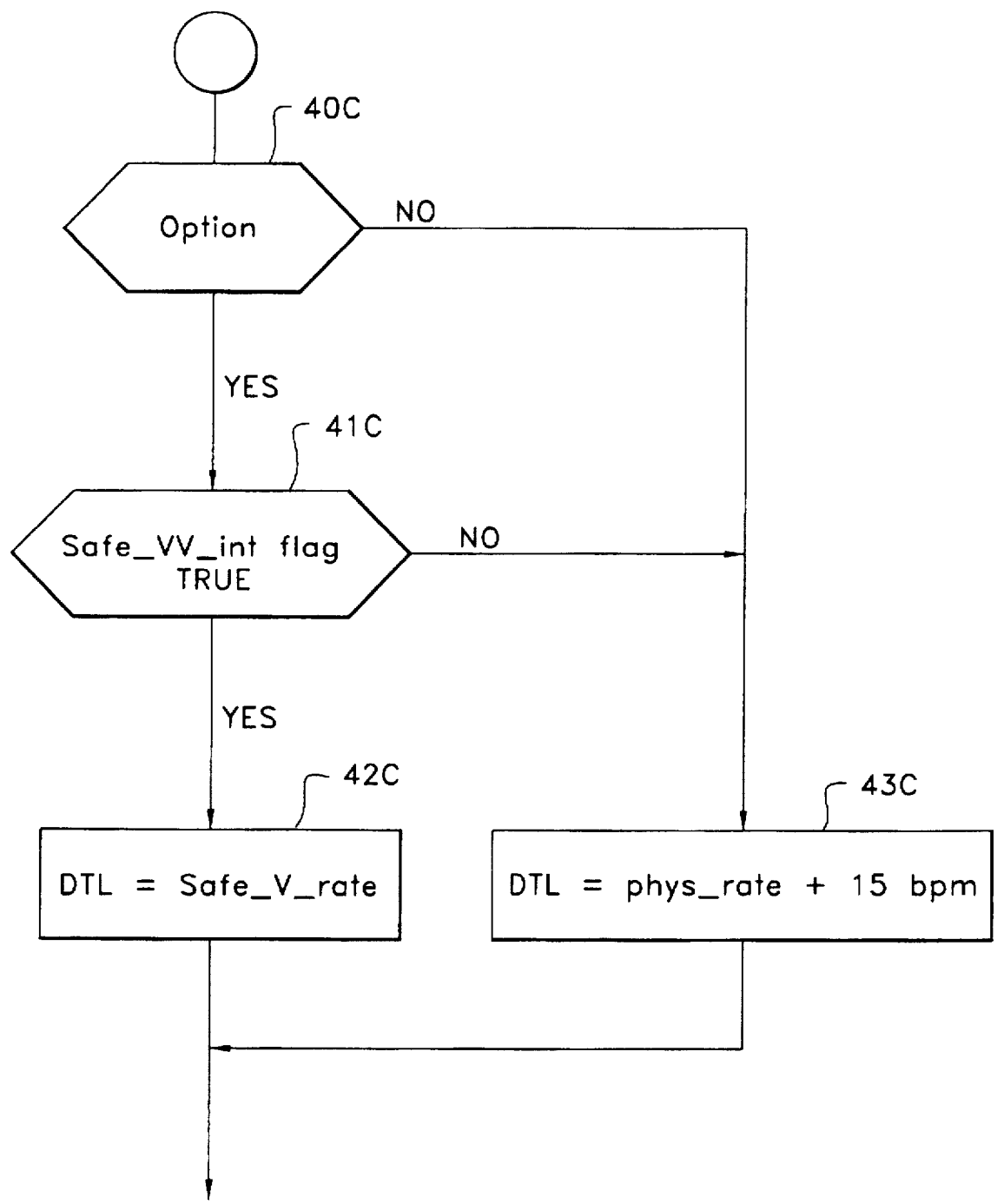
FIG. 4C is a flow diagram showing determination of the dynamic tracking limit in accordance with an optional embodiment of this invention.

Referring now to FIG. 4C, there is shown a flow diagram for optionally setting DTL to the Safe_V_rate. It is to be understood that this effectively removes the difference between PAC tracking and normal tracking, i.e., the criteria for safe PAC tracking are used for all tracking opportunities. At 40C, it is determined whether the option has been programmed. If not, DTL is set to phys_rate plus 15 bpm, i.e., it is set in the normal way. But, if the option is programmed, the routine goes to block 41C, where it is determined whether the safe_VV_int flag is set to TRUE. If yes, then at 42C the dynamic tracking limit is set equal to safe_V_rate, meaning that the safe_V_rate is substituted as the tracking limit. Alternately, if the flag is set to FALSE, at 43C the dynamic tracking limit is calculated as the phys_rate+15 bpm.

Figure 5:
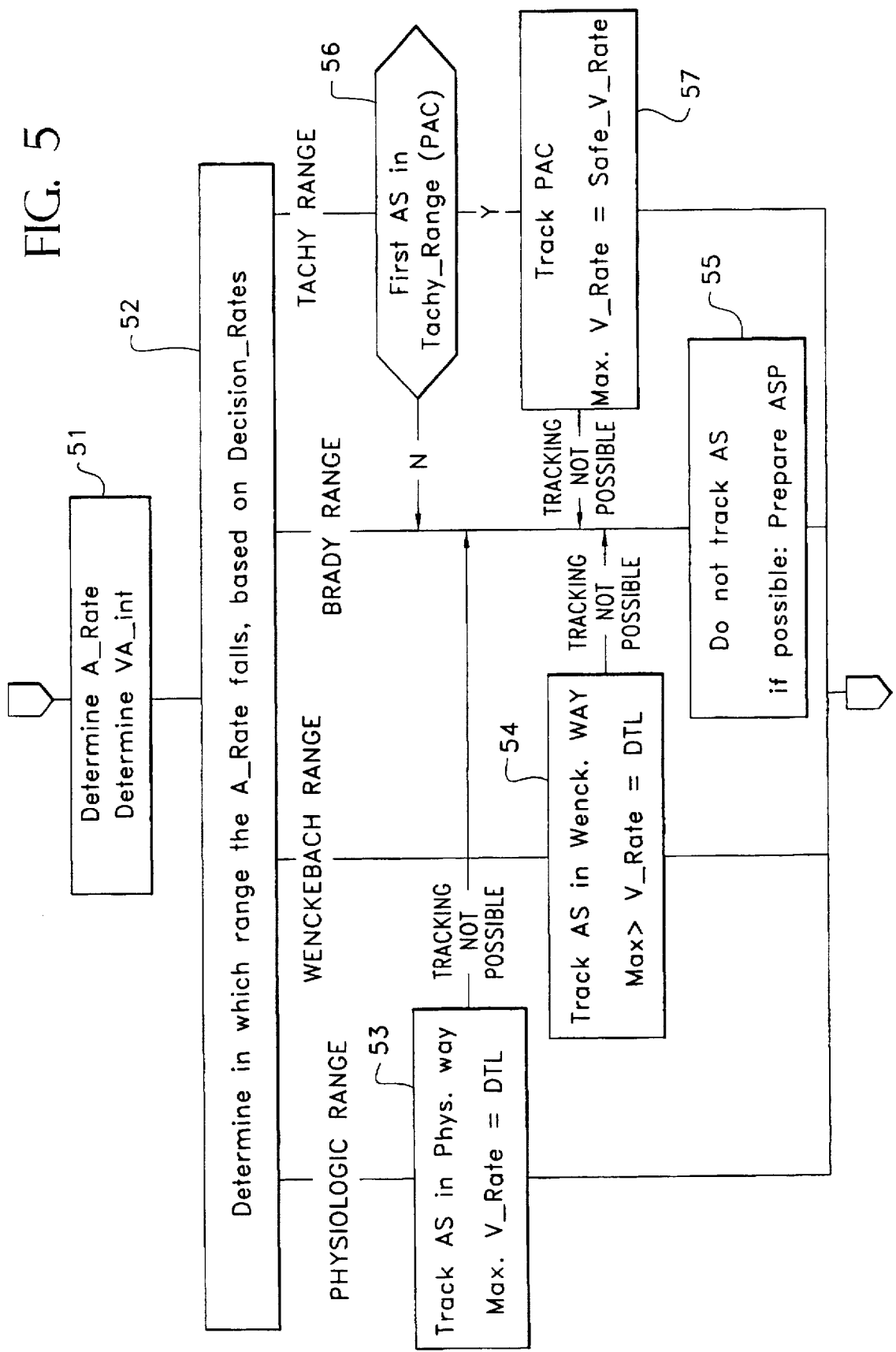
FIG. 5 is a flow diagram illustrating the primary steps in handling an atrial sense (AS) so as to determine appropriate pacemaker response.

Referring now to FIG. 5, there is shown a flow diagram for atrial sense handling. At 51, the atrial rate and the VA_interval are determined. Following this, at 52, and knowing the atrial rate, the pacemaker determines in which range the atrial rate falls, based on the previously determined decision rates. Reference is made to U.S. Pat. No. 5,247,930, for a full discussion of this determination. Thus, the atrial sense can be determined within the physiological range, the Wenckebach range, the brady range, or the tachy range. If the A_sense is within the physiological range, the routine goes to block 53 and tracks the AS in a way corresponding to a physiological sense, where the maximum ventricular rate is equal to the dynamic tracking limit. If tracking is not possible, the routine then goes to block 55, where an atrial sync pulse (ASP) is prepared if this is determined to be possible. If the AS was in the Wenckebach range, the routine goes to block 54, and tracks the atrial sense in accordance with Wenckebach rules, if possible. If the AS was in the brady range, there is no tracking, and an ASP is prepared if this is determined to be possible. Lastly, if the AS is in the tachy range, the routine goes to 56 and determines whether it is the first AS in the tachy range, i.e., was it a PAC? If no, the routine branches to block 55, but if yes, the routine goes to block 57 and tracks the PAC if possible, using the safe_V_rate as the maximum V_rate.

Figure 6:
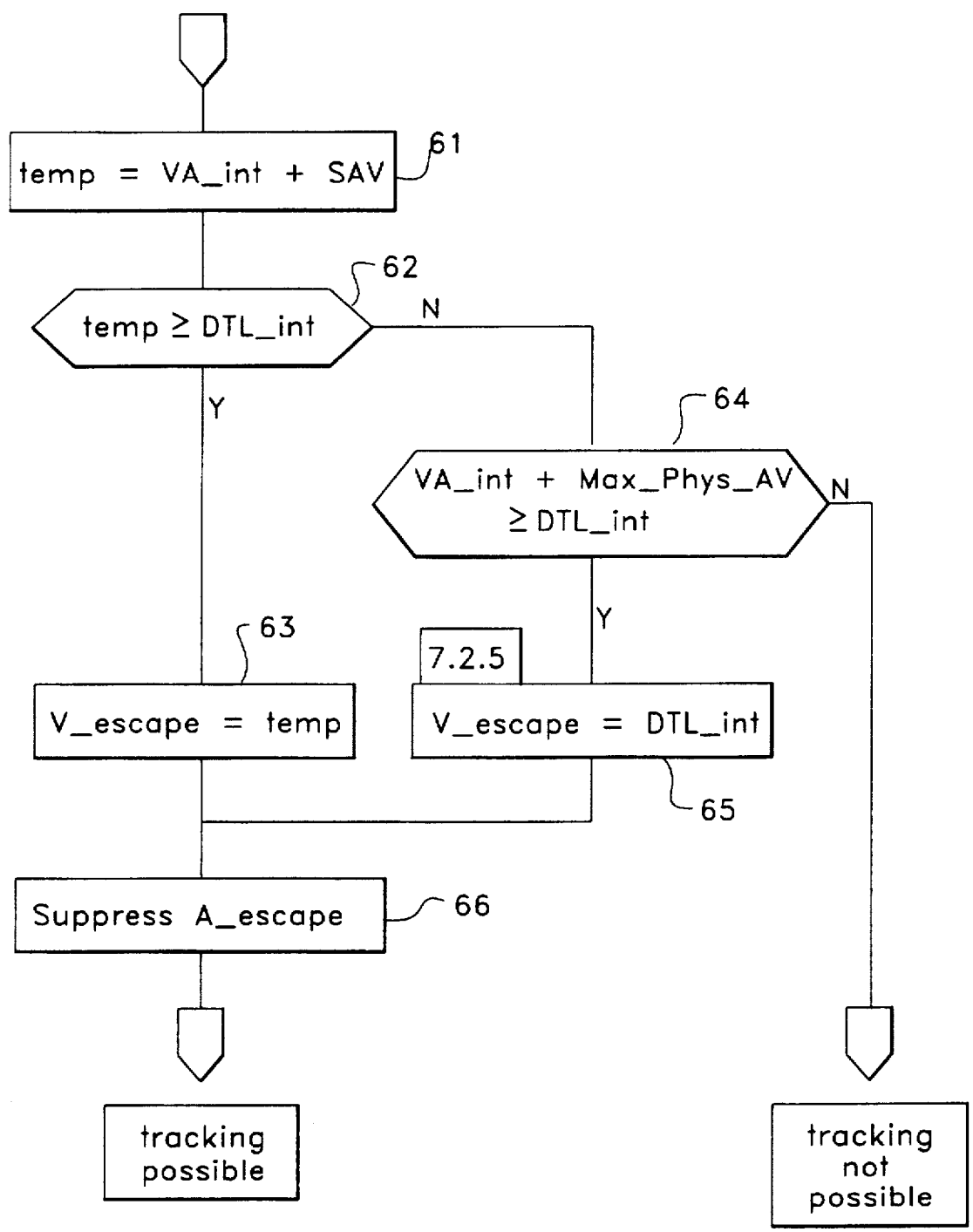
FIG. 6 is a flow diagram illustrating tracking an AS which is found to be physiologic.

Referring now to FIG. 6, there is shown a block diagram of the manner of tracking an AS that is physiological. At step 61, a temporary variable is set up equal to VA_int+SAV, where SAV is the AV interval following a sense. At 67, this temporary variable is compared to the dynamic tracking limit interval (DTL_int). If it is greater, meaning that the rate is lower than the DTL, the routine goes to 63 and sets V_escape equal to the temporary variable, and then at 66 suppresses A_escape, which means that the scheduled A-pace is suppressed. However, if at 67 the variable is not greater than or equal to DTL_int, the routine goes to 64 and compares VA_int+MAX_phys_AV with DTL_int, to see if tracking can be done using the maximum permissible AV interval. If no, the routine exits, since tracking is not possible. If yes, the escape is set equal to DTL_int at 65 and then A_escape is suppressed at 66. Thus, for a physiological atrial sense, tracking is carried out as long as the resulting ventricular interval corresponds to a rate no greater than the dynamic tracking limit, as illustrated in FIG. 2A.

Figure 7:
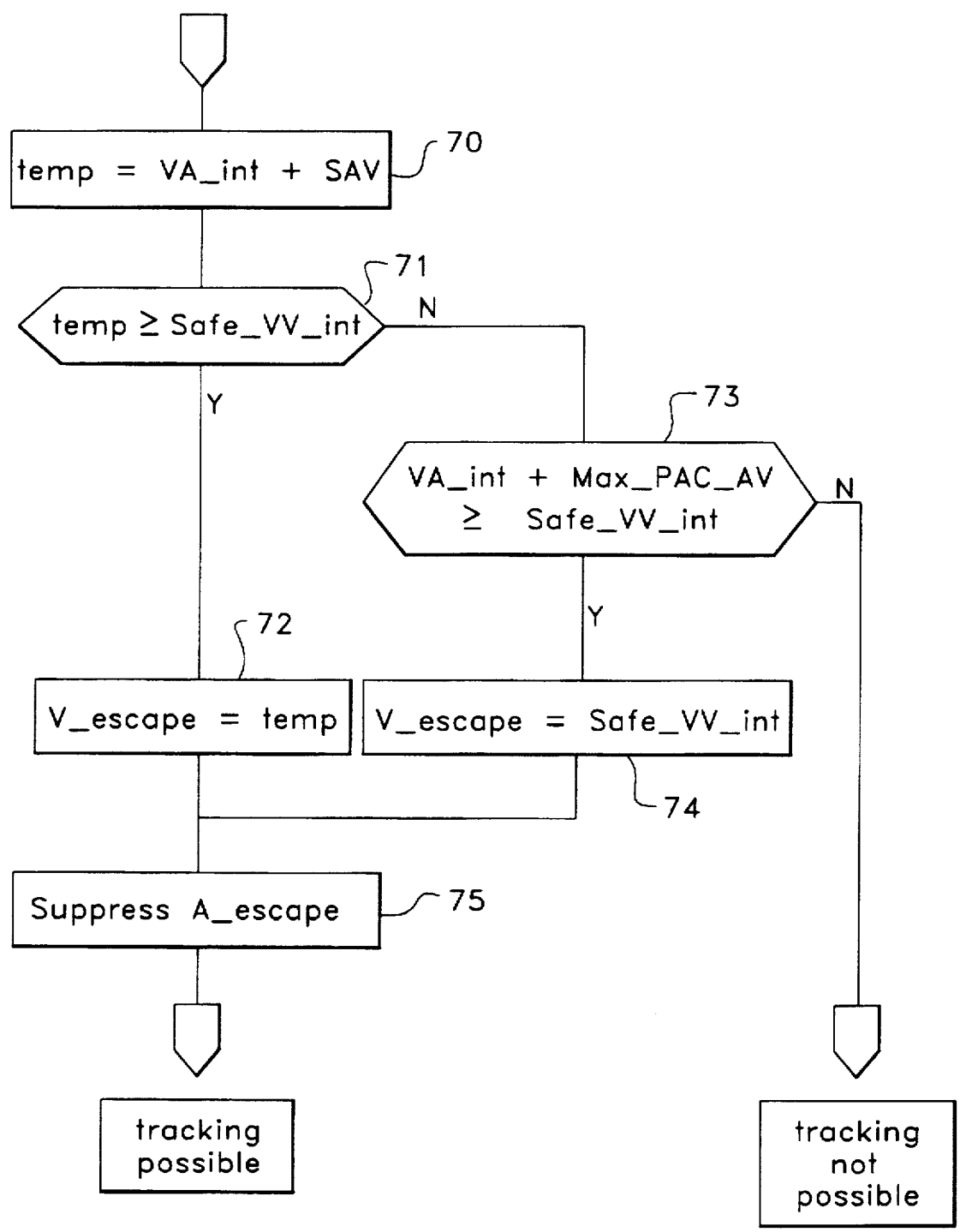
FIG. 7 is a flow diagram illustrating the primary steps in tracking a PAC in accordance with a first preferred embodiment of this invention.

Referring now to FIG. 7, there is shown a block diagram of the method of tracking a PAC in accordance with a first preferred embodiment of this invention. Note that in this embodiment, the pacemaker does not look for a T-wave in the current cycle, but rather uses QT data available from one or more prior cycles. At 70, the temporary variable is set equal to AV_int+SAV, and at 71 this variable is compared to Safe_VV_int, which has been set in accordance with the flow diagram of FIG. 4B. If the variable is greater, the V_escape is set equal to the temporary variable at 72, and at 75 A_escape is suppressed. However, if the answer at 71 is no, this means that the calculated time would come too close to the T wave, and thus would not be safe. The routine branches to block 73, and determines whether VA_int+MAX_PAC_AV is greater than Safe_VV_int. If yes, tracking is possible, and at 74 V_escape is set equal to Safe_VV_int; if no, tracking is not possible and the routine exits to block 55 of FIG. 5.

Figure 8:
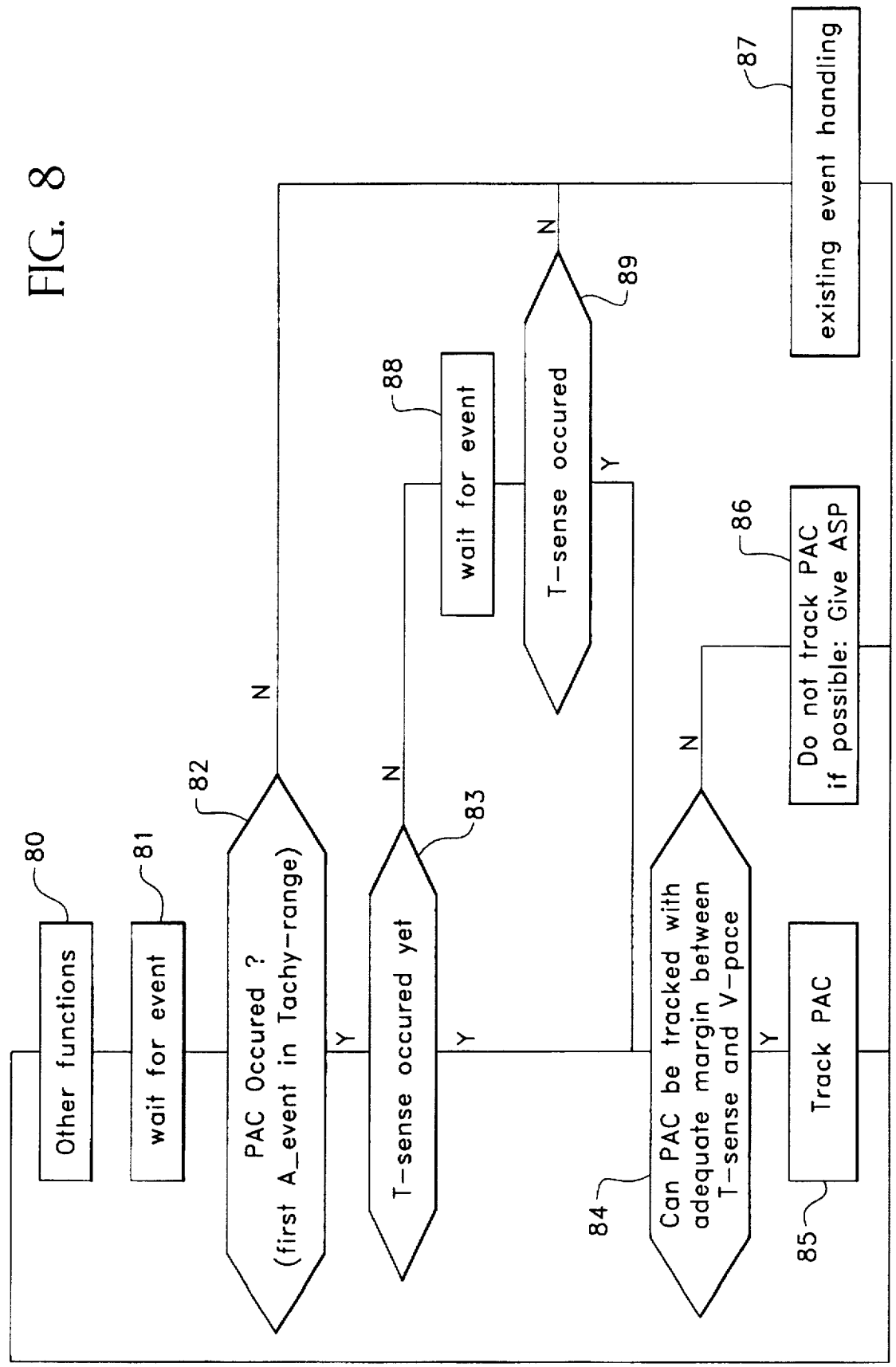
FIG. 8 is a flow diagram illustrating the principle, or logic of a second preferred embodiment of this invention, wherein reaction to a PAC is made dependent upon sensing of a T-wave in the cycle during which the PAC has occurred.

In a second preferred embodiment of this invention, the decision as to whether the PAC can be safely tracked is based upon sensing or not sensing a T-wave in the present cycle. Referring to FIG. 8, there is shown a flow diagram of a cyclical operation illustrating the principle of this embodiment. After other functions are performed at 80, at 81 the pacemaker waits for an event. At 82, it is determined whether a PAC has occurred, i.e., has there been an AS which is first such atrial sense in the tachy range rates? If no, the routine goes to 87 and handles the event appropriately. If yes, at 83 the pacemaker determines whether a T_sense has yet occurred. If yes, meaning that the PAC occurred after the T_sense, the routine goes to 84 and determines whether the PAC can be tracked with an adequate margin between the T_sense and the pace. This margin, referred to previously as a safety margin, can be a programmed or a dynamic variable. If the answer is no, the routine branches to 86 and determines whether an atrial sync pulse (ASP) can be delivered. If, however, at 84 the answer is yes, the routine tracks the PAC, as indicated at 85.

Returning to 83, if it is determined that a T_sense has not yet occurred, the routine goes to 85 and waits for an event, e.g., a T_sense or a timeout of the ventricular escape interval. At 89, if the next event has been a T_sense, the routine branches to 84 to determine whether the PAC can be safely tracked. However, if the next event is not a T_sense, it is concluded that the PAC cannot be tracked, and the routine branches to 87.

Figure 9:
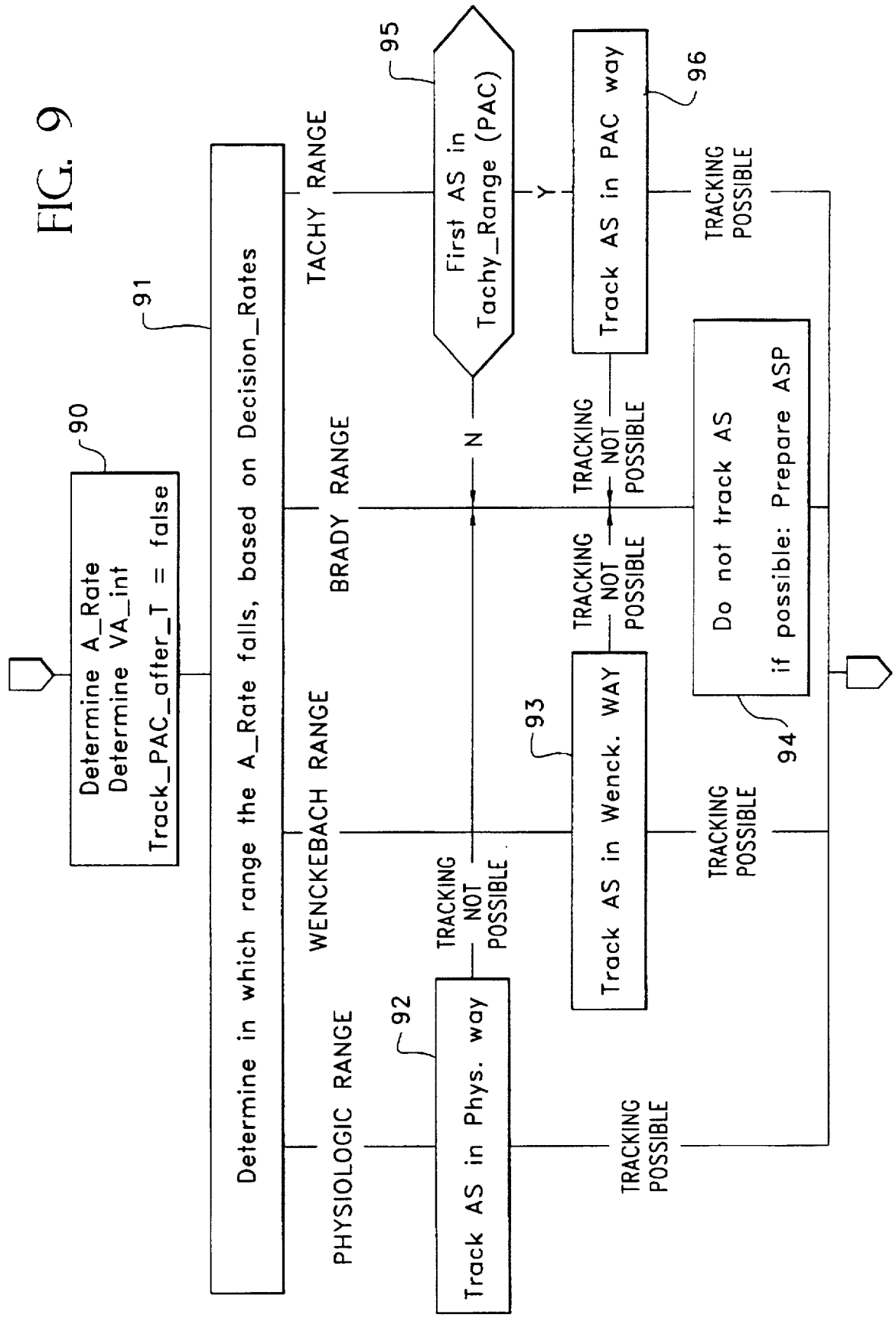
FIG. 9 is a flow diagram of the primary steps taken in atrial sense handling in accordance with the second preferred embodiment of this invention.

In this second preferred embodiment, as indicated above in connection with the discussion of FIG. 3, block 33, the flag for Track_PAC_after_T is set false; and at FIG. 4A, block 42, there is no calculation of the Safe_V_rate at the start of the cycle. With these exceptions, FIGS. 3 and 4A as discussed above apply to this second preferred embodiment. Referring to FIG. 9, there is shown a flow diagram for handling an atrial sense. At block 90, the timing of the AS is analyzed to determine the atrial rate and the VA interval; and the Track_PAC_after_T flag is set FALSE. At 91, the pacemaker determines in which range the atrial rate falls, based on the Decision_Rates. Atrial rates in the physiological range are handled at 92 in the same manner as discussed above; atrial rates in the Wenkebach range are again handled at block 93; and atrial rates in the brady range are handled in the same manner at block 94. Atrial rates in the tachy range cause the pacemaker to go to the operation indicated at 95, to determine whether this is the first AS in the tachy range and thus is identified as a PAC. If yes, the routine goes to 96 and attempts to track the atrial sense in a special PAC way, as is set forth in detail in FIG. 10.

Figure 10:
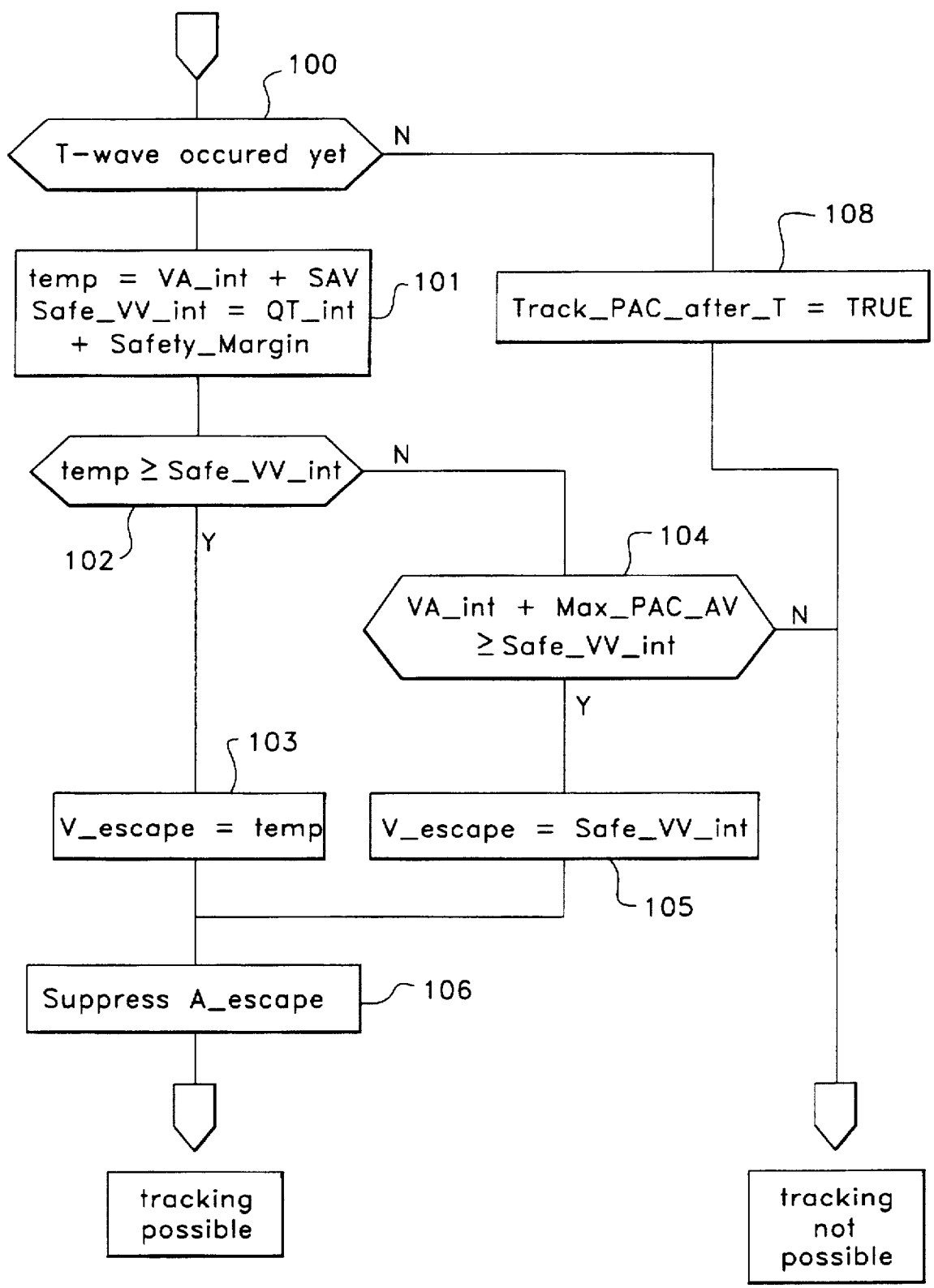
FIG. 10 is a flow diagram of the primary steps taken in tracking an atrial sense which has been determined to be a PAC, in accordance with the second preferred embodiment of this invention.

At block 100 of FIG. 10, it is determined whether the T-wave has occurred yet. If no, the routine goes to block 108, and sets the Track_PAC_after_T flag TRUE. Since tracking is not yet possible, the routine exits and waits for the next event. As indicated in the following discussion of FIG. 11, if the next event is a T-wave, the pacemaker can try to deliver a tracking ventricular pace pulse at a safe margin after the T-wave.

Returning to step 100, if the T-wave has occurred, at 101 the temporary variable is set equal to VA_int+SAV, and Safe_VV_int set equal to QT_int+Safety_Margin. AT 102, it is determined whether the temporary variable is equal to or greater than Safe_VV_int. If yes, the ventricular escape interval is set equal to the temporary variable at 103. The atrial escape interval is then reset at 106, and the routine exits, waiting for the next event. However, if the answer at 102 is no, the routine branches to 104, and determines whether VA_int+MAX_PAC_AV is equal to or greater than Safe_VV_int. If no, tracking is not possible, and the routine exits. If yes, V_escape is set equal to Safe_VV_int, so tracking will occur with the maximum permissible AV interval for a PAC.

Figure 11:
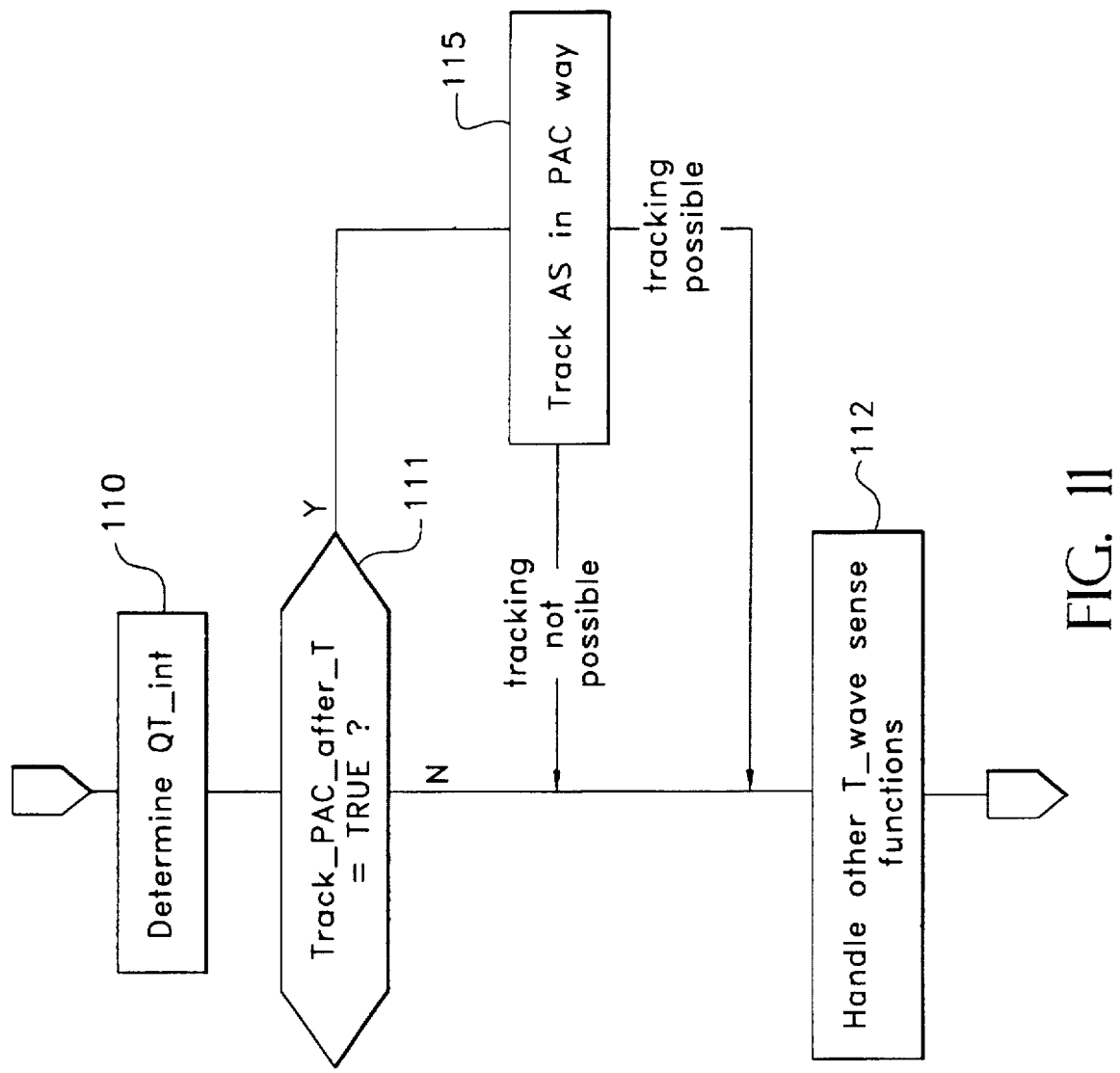
FIG. 11 is a flow diagram illustrating handling of a T-wave sense in accordance with the second preferred embodiment of this invention.

Referring to FIG. 11, there is shown a routine for handling a TS, i.e., a sensed T_wave. As illustrated in FIG. 3, where this routine is identified at block 37, it is entered after a T_wave_sense. At 110, the QT_int is determined. At 111, it is determined whether the Track_PAC_after_T flag is TRUE. If yes, the routine goes to 115 and again attempts to track the AS in a PAC way, as seen at FIG. 10, where now the answer at block 100 is YES. If, at 111, the flag is FALSE, then there is no call for PAC tracking, and the routine exits after handling other T-wave sense functions as indicated at 112.

There has thus been illustrated a system and method for determining when a PAC can be tracked by delivering a ventricular pace pulse synchronized to the PAC. This determination is made based upon either the time of the T-wave in the same cardiac cycle with the PAC, or a predicted time of the T-wave based on the preceding beats, together with a safety margin interval calculated to ensure that the synchronized ventricular pace pulse is delivered only at safe time relative to the ventricular vulnerable phase.

We claim:

1. An implantable dual chamber pacemaker system for pacing the heart of a patient, comprising atrial sense means for sensing atrial beats from the patient's heart, ventricular generator means for generating and delivering ventricular pace pulses to the patient, tracking means for enabling said ventricular generator means to track sensed atrial beats by delivering ventricular pace pulses in timed relation to said sensed atrial beats, QT_int means for obtaining measures of the QT interval between delivered ventricular pace pulses and respective following T-waves, safety means for determining a safety interval as a function of one or more of said QT interval measures, and wherein said tracking means comprises tracking limit means for limiting the rate of said tracking to correspond to said safety interval.

2. The system as described in claim 1, comprising reliability means for determining when reliable QT interval measures have not been obtained, and default means for limiting said tracking to a default rate when reliable QT interval measures have not been obtained.

3. The system as described in claim 2, comprising DTL means for determining the patient's physiological atrial rate and for setting said default rate as a function of said physiological rate.

4. The system as described in claim 1, wherein said safety means comprises means for determining a running average of the patient's QT interval, and means for setting said safety interval as said running average plus a predetermined safety margin.

5. The system as described in claim 1, wherein said safety means comprises means for determining the QT interval of the patient's last cardiac cycle, and means for setting said safety interval as said last QT interval plus a predetermined safety margin.

6. The system as described in claim 1, wherein said safety means comprises means for determining a safe QT interval as a function of one or more of said QT interval measures, margin means for determining a safety margin, and means for calculating said safety interval as the sum of said safe QT interval and said safety margin.

7. The system as described in claim 1, wherein said safety means comprises means for determining a safety margin as a function of pacing rate and means for determining said safety interval as a function of said safety margin.

8. The system as described in claim 1, further comprising ventricular sense means for sensing spontaneous ventricular beats, and wherein said QT_int means further comprises means for obtaining measures of the QT interval between sensed spontaneous ventricular beats and respective following T-waves.

9. An implantable dual chamber pacemaker system for pacing a patient's heart, comprising atrial sense means for sensing atrial signals from the patient's atrium, ventricular pace means for generating and delivering pace pulses to the patient's ventricle, tracking means for enabling said ventricular pace means to track sensed atrial signals by delivering ventricular pace pulses in timed relation to said sensed atrial signals, T sense means for determining when a T-wave has occurred, PAC means for determining when a sensed atrial signal represents a PAC, safety margin means for determining the time out of a predetermined safety margin interval following a said sensed T-wave, and wherein said tracking means has safety means for enabling delivery of a ventricular pace pulse following a PAC only when delivery of the ventricular pace pulse occurs at or after time out of said safety margin interval.

10. The system as described in claim 9, wherein said safety margin means comprises means for determining said safety margin interval as a function of pacing rate.

11. The system as described in claim 9, wherein said tracking means comprises means for determining an AV interval and for delivering a said pace pulse at time out of a said AV interval after a sensed atrial signal, and further comprising means for lengthening said AV interval up to a predetermined maximum value.

12. A dual chamber pacing system for cardiac pacing of a patient, comprising sensing means for sensing atrial and ventricular signals, ventricular pacing means for delivering a ventricular pace pulse in a calculated tracking relationship to a sensed atrial signal, T means for sensing the occurrence and timing of T-waves, PAC means for determining when a sensed atrial signal represents a PAC, and safety means for controlling when a said tracking pace pulse can be delivered, said safety means having prevent means for preventing delivery of a pace pulse tracking a PAC unless it is delivered at least a predetermined safety interval after the T-wave that occurs in the cycle in which the PAC occurs.

13. A method of providing for safe tracking of PACs with a dual chamber pacemaker system, comprising:

determining the occurrence of a PAC following a last ventricular event;

obtaining an indication of the time of a T-wave following said last ventricular event;

determining the time of delivery of a next ventricular pace pulse synchronized to the PAC; and delivering said next synchronized pace pulse only if it can be delivered at a safe interval following said T-wave.

14. The method as described in claim 13, comprising sensing said T-wave.

15. The method as described in claim 13, comprising sensing QT intervals each cycle, and determining the time of the T-wave as a function of one or more sensed QT intervals from prior cycles.

16. The method as described in claim 15, comprising calculating a QT running average of said sensed QT intervals, and determining said T-wave time as the time of said last ventricular event plus said QT running average.

17. The method as described in claim 13, comprising obtaining an indication of the time of a T-wave following a delivered ventricular pace pulse.

18. The method as described in claim 13, comprising sensing natural ventricular beats, and obtaining an indication of the time of a T-wave following a sensed natural ventricular beat.

19. An implantable dual chamber pacemaker system for pacing the heart of a patient, comprising atrial sense means for sensing atrial beats from the patient's heart, ventricular sense means for sensing spontaneous ventricular beats, ventricular generator means for generating and delivering ventricular pace pulses to the patient, tracking means for enabling said ventricular generator means to track sensed atrial beats by delivering ventricular pace pulses in timed relation to said sensed atrial beats, QT_int means for obtaining measures of the QT interval between delivered or sensed ventricular pace pulses and respective following T-waves, safety means for determining a safety interval as a function of one or more of said QT interval measures, and wherein said tracking means comprises tracking limit means for limiting the rate of said tracking to correspond to said safety interval.

20. The system as described in claim 19, comprising PAC means for determining the occurrence of a PAC following a last ventricular event, means for determining the time of delivery of a next ventricular pace pulse synchronized to the PAC, and wherein said tracking means comprises PAC tracking means for enabling delivery of said next synchronized ventricular pace pulse only if it can be delivered at at least said safety interval following the last ventricular event.

* * * * *